(12) United States Patent
Thede

(10) Patent No.: US 6,558,335 B1
(45) Date of Patent: May 6, 2003

(54) WRIST-MOUNTED BLOOD PRESSURE MEASUREMENT DEVICE

(75) Inventor: Roger C. Thede, Afton, MN (US)

(73) Assignee: Medwave, Inc, Danvers, MA (US)

( * ) Notice: Subject to any disclaimer, the term of this patent is extended or adjusted under 35 U.S.C. 154(b) by 184 days.

(21) Appl. No.: 09/721,216

(22) Filed: Nov. 22, 2000

(51) Int. Cl.⁷ .................................................. A61B 5/02
(52) U.S. Cl. ........................ 600/503; 600/485; 600/490
(58) Field of Search ................................. 600/503, 485, 600/490, 500, 501, 502, 499, 491, 488, 481

(56) References Cited

U.S. PATENT DOCUMENTS

| | | | |
|---|---|---|---|
| 4,409,983 A | | 10/1983 | Albert |
| 4,858,615 A | | 8/1989 | Meinema |
| 5,240,007 A | * | 8/1993 | Pytel et al. |
| 5,241,964 A | | 9/1993 | McQuilkin |
| 5,243,992 A | * | 9/1993 | Eckerle et al. |
| 5,269,312 A | | 12/1993 | Kawamura et al. |
| 5,271,405 A | * | 12/1993 | Boyer et al. |
| 5,425,375 A | | 6/1995 | Chin et al. |
| 5,450,852 A | | 9/1995 | Archibald et al. |
| 5,494,043 A | | 2/1996 | O'Sullivan et al. |
| 5,566,676 A | | 10/1996 | Rosenfeldt et al. |
| 5,617,867 A | * | 4/1997 | Butterfield et al. |
| 5,640,964 A | | 6/1997 | Archibald et al. |
| 5,642,733 A | | 7/1997 | Archibald et al. |
| 5,649,542 A | | 7/1997 | Archibald et al. |
| 5,687,732 A | | 11/1997 | Inagaki et al. ............... 128/672 |
| 5,720,292 A | | 2/1998 | Poliac |
| 5,722,414 A | | 3/1998 | Archibald et al. |
| 5,738,103 A | | 4/1998 | Poliac |
| 5,749,366 A | | 5/1998 | Odagiri et al. |
| 5,779,630 A | | 7/1998 | Fein et al. |
| 5,797,850 A | | 8/1998 | Archibald et al. |
| 5,832,924 A | | 11/1998 | Archibald et al. |
| 5,857,976 A | | 1/1999 | Quinn et al. |
| 5,908,027 A | * | 6/1999 | Butterfield et al. |
| 5,938,618 A | | 8/1999 | Archibald et al. .......... 600/485 |
| 5,941,828 A | | 8/1999 | Archibald et al. |
| 5,971,930 A | | 10/1999 | Elghazzawi |
| 6,132,382 A | | 10/2000 | Archibald et al. .......... 600/485 |
| 6,290,650 B1 | * | 9/2001 | Butterfield et al. |

* cited by examiner

Primary Examiner—Max Hindenburg
Assistant Examiner—Navin Natnithithadha
(74) Attorney, Agent, or Firm—Kinney & Lange P.A.

(57) ABSTRACT

A device for sensing blood pressure of an underlying artery of a patient includes a housing having a sensing region and a pivot region. The sensing region is pivotable about the pivot region in response to a hold down pressure applied at the sensing region by a user. The device includes a sensor interface assembly that is supported by the sensing region. The sensor interface assembly includes a sensing surface suited for engaging tissue adjacent the artery for sensing pressure from the artery. A wrist connection holds the housing adjacent the patient's wrist.

26 Claims, 4 Drawing Sheets

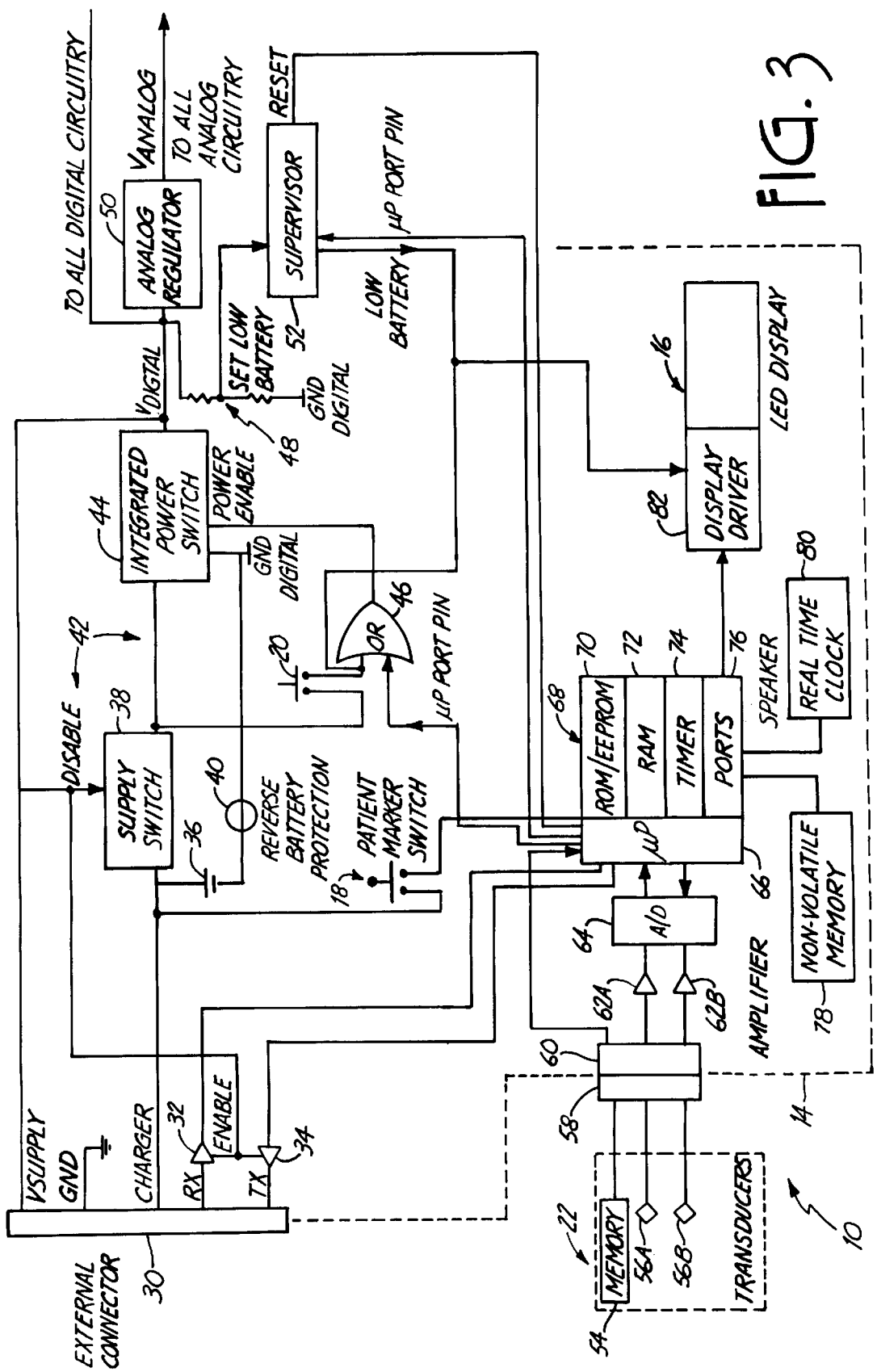

WRIST-MOUNTED BLOOD PRESSURE MEASUREMENT DEVICE

BACKGROUND OF THE INVENTION

The present invention relates to systems for measuring arterial blood pressure. In particular, the invention relates to a method and apparatus for conveniently positioning a non-invasive blood pressure measurement device over an underlying artery for accurate measurement.

Blood pressure has been typically measured by one of four basic methods: invasive, oscillometric, auscultatory and tonometric. The invasive method, otherwise known as an arterial line (A-Line), involves insertion of a needle into the artery. A transducer connected by a fluid column is used to determine exact arterial pressure. With proper instrumentation, systolic, mean and diastolic pressure may be determined. This method is difficult to set up, is expensive and involves medical risks. Set up of the invasive or A-line method poses problems. Resonance often occurs and causes significant errors. Also, if a blood clot forms on the end of the catheter, or the end of the catheter is located against the arterial wall, a large error may result. To eliminate or reduce these errors, the set up must be adjusted frequently. A skilled medical practitioner is required to insert the needle into the artery. This contributes to the expense of this method. Medical complications are also possible, such as infection or nerve damage.

The other methods of measuring blood pressure are non-invasive. The oscillometric method measures the amplitude of pressure oscillations in an inflated cuff. The cuff is placed against a cooperating artery of the patient and thereafter pressurized or inflated to a predetermined amount. The cuff is then deflated slowly and the pressure within the cuff is continually monitored. As the cuff is deflated, the pressure within the cuff exhibits a pressure versus time waveform. The waveform can be separated into two components, a decaying component and an oscillating component. The decaying component represents the mean of the cuff pressure while the oscillating component represents the cardiac cycle. The oscillating component is in the form of an envelope starting at zero when the cuff is inflated to a level beyond the patient's systolic blood pressure and then increasing to a peak value where the mean pressure of the cuff is equal to the patient's mean blood pressure. Once the envelope increases to a peak value, the envelope then decays as the cuff pressure continues to decrease.

Systolic blood pressure, mean blood pressure and diastolic blood pressure values can be obtained from the data obtained by monitoring the pressure within the cuff while the cuff is slowly deflated. The mean blood pressure value is the pressure on the decaying mean of the cuff pressure that corresponds in time to the peak of the envelope. Systolic blood pressure is generally estimated as the pressure on the decaying mean of the cuff prior to the peak of the envelope that corresponds in time to where the amplitude of the envelope is equal to a ratio of the peak amplitude. Generally, systolic blood pressure is the pressure on the decaying mean of the cuff prior to the peak of the envelope where the amplitude of the envelope is 0.57 to 0.45 of the peak amplitude. Similarly, diastolic blood pressure is the pressure on the decaying mean of the cuff after the peak of the envelope that corresponds in time to where the amplitude of the envelope is equal to a ratio of the peak amplitude. Generally, diastolic blood pressure is conventionally estimated as the pressure on the decaying mean of the cuff after the peak where the amplitude of the envelope is equal to 0.82 to 0.74 of the peak amplitude.

The auscultatory method also involves inflation of a cuff placed around a cooperating artery of the patient. Upon inflation of the cuff, the cuff is permitted to deflate. Systolic pressure is indicated when Korotkoff sounds begin to occur as the cuff is deflated. Diastolic pressure is indicated when the Korotkoff sounds become muffled or disappear. The auscultatory method can only be used to determine systolic and diastolic pressures.

Because both the oscillometric and the auscultatory methods require inflation of a cuff, performing frequent measurements is difficult. The frequency of measurement is limited by the time required to comfortably inflate the cuff and the time required to deflate the cuff as measurements are made. Because the cuff is inflated around a relatively large area surrounding the artery, inflation and deflation of the cuff is uncomfortable to the patient. As a result, the oscillometric and auscultatory methods are not suitable for long periods of repetitive use.

Both the oscillometric and auscultatory methods lack accuracy and consistency for determining systolic and diastolic pressure values. The oscillometric method applies an arbitrary ratio to determine systolic and diastolic pressure values. As a result, the oscillometric method does not produce blood pressure values that agree with the more direct and generally more accurate blood pressure values obtained from the A-line method. Furthermore, because the signal from the cuff is very low compared to the mean pressure of the cuff, a small amount of noise can cause a large change in results and result in inaccurate measured blood pressure values. Similarly, the auscultatory method requires a judgment to be made as to when the Korotkoff sounds start and when they stop. This detection is made when the Korotkoff sound is at its very lowest. As a result, the auscultatory method is subject to inaccuracies due to low signal-to-noise ratio.

The fourth method used to determine arterial blood pressure has been tonometry. The tonometric method typically involves a transducer including an array of pressure sensitive elements positioned over a superficial artery. Hold down forces are applied to the transducer so as to flatten the wall of the underlying artery without occluding the artery. The pressure sensitive elements in the array typically have at least one dimension smaller than the lumen of the underlying artery in which blood pressure is measured. The transducer is positioned such that at least one of the individual pressure sensitive elements is over at least a portion of the underlying artery. The output from one of the pressure sensitive elements is selected for monitoring blood pressure. The pressure measured by the selected pressure sensitive element is dependent upon the hold down pressure used to press the transducer against the skin of the patient. These tonometric systems measure a reference pressure directly from the wrist and correlate this with arterial pressure. However, because the ratio of pressure outside the artery to the pressure inside the artery, known as gain, must be known and constant, tonometric systems are not reliable. Furthermore, if a patient moves, recalibration of the tonometric system is required because the system may experience a change in gains. Because the accuracy of these tonometric systems depends upon the accurate positioning of the individual pressure sensitive element over the underlying artery, placement of the transducer is critical. Consequently, placement of the transducer with these tonometric systems is time-consuming and prone to error.

The oscillometric, auscultatory and tonometric methods measure and detect blood pressure by sensing force or displacement caused by blood pressure pulses as the underlying artery is compressed or flattened. The blood pressure is sensed by measuring forces exerted by blood pressure pulses in a direction perpendicular to the underlying artery. However, with these methods, the blood pressure pulse also exerts forces parallel to the underlying artery as the blood pressure pulses cross the edges of the sensor which is pressed against the skin overlying the underlying artery of the patient. In particular, with the oscillometric and the auscultatory methods, parallel forces are exerted on the edges or sides of the cuff. With the tonometric method, parallel forces are exerted on the edges of the transducer. These parallel forces exerted upon the sensor by the blood pressure pulses create a pressure gradient across the pressure sensitive elements. This uneven pressure gradient creates at least two different pressures, one pressure at the edge of the pressure sensitive element and a second pressure directly beneath the pressure sensitive element. As a result, the oscillometric, auscultatory and tonometric methods produce inaccurate and inconsistent blood pressure measurements.

There has been a continuing need for devices which will measure blood pressure non-invasively, with accuracy comparable to invasive methods. Medwave, Inc. the assignee of the present invention, has developed non-invasive blood pressure measurement methods and devices which are described in the following United States patents, hereby incorporated by reference: U.S. Pat. No. 5,649,542 entitled CONTINUOUS NON-INVASIVE BLOOD PRESSURE MONITORING SYSTEM; U.S. Pat. No. 5,450,852 entitled CONTINUOUS NON-INVASIVE PRESSURE MONITORING SYSTEM; U.S. Pat. No. 5,640,964 entitled WRIST MOUNTED BLOOD PRESSURE SENSOR; U.S. Pat. No. 5,720,292 entitled BEAT ONSET DETECTOR; U.S. Pat. No. 5,738,103 entitled SEGMENTED ESTIMATION METHOD; U.S. Pat. No. 5,722,414 entitled CONTINUOUS NON-INVASIVE BLOOD PRESSURE MONITORING SYSTEM; U.S. Pat. No. 5,642,733 entitled BLOOD PRESSURE SENSOR LOCATOR; U.S. Pat. No. 5,797,850 entitled METHOD AND APPARATUS FOR CALCULATING BLOOD PRESSURE OF AN ARTERY; and U.S. Pat. No. 5,941,828 entitled HAND-HELD NON-INVASIVE BLOOD PRESSURE MEASUREMENT DEVICE.

As described in these patents, blood pressure is determined by sensing pressure waveform data derived from an artery. A pressure sensing device includes a sensing chamber with a diaphragm which is positioned over the artery. A transducer coupled to the sensing chamber senses pressure within the chamber. A flexible body conformable wall is located adjacent to (and preferably surrounding) the sensing chamber. The wall is isolated from the sensing chamber and applies force to the artery while preventing pressure in a direction generally parallel to the artery from being applied to the sensing chamber. As varying pressure is applied to the artery by the sensing chamber, pressure waveforms are sensed by the transducer to produce sensed pressure waveform data. The varying pressure may be applied automatically in a predetermined pattern, or may be applied manually.

The sensed pressure waveform data is analyzed to determine waveform parameters which relate to the shape of the sensed pressure waveforms. One or more blood pressure values are derived based upon the waveform parameters. The Medwave blood pressure measurement devices include both automated devices for continually monitoring blood pressure (such as in a hospital setting) and hand-held devices which can be used by a physician or nurse, or by a patient when desired. These devices represent an important improvement in the field of non-invasive blood pressure measurement. Still further improvements, specifically with respect to convenient and accurate placement of the measurement device over an underlying artery, are highly desirable.

BRIEF SUMMARY OF THE INVENTION

The present invention is a wrist-mounted blood pressure measurement device that consistently positions a sensor assembly over an underlying artery, and through a pivoting or cantilever type action, provides an axial force to the underlying artery.

In a preferred embodiment, the device for sensing blood pressure of an underlying artery of a patient according to the present invention includes a housing having a sensing region and a pivot region. The sensing region is pivotable about the pivot region in response to a hold down pressure applied at the sensing region by a user. The device includes a sensor interface assembly that is supported by the sensing region. The sensor interface assembly includes a sensing surface suited for engaging tissue adjacent the artery for sensing pressure from the artery. A wrist connection holds the housing adjacent the patient's wrist.

BRIEF DESCRIPTION OF THE DRAWINGS

FIG. 3 is an electrical block diagram of the blood pressure measurement device of the present invention.

DETAILED DESCRIPTION

Figure 1:
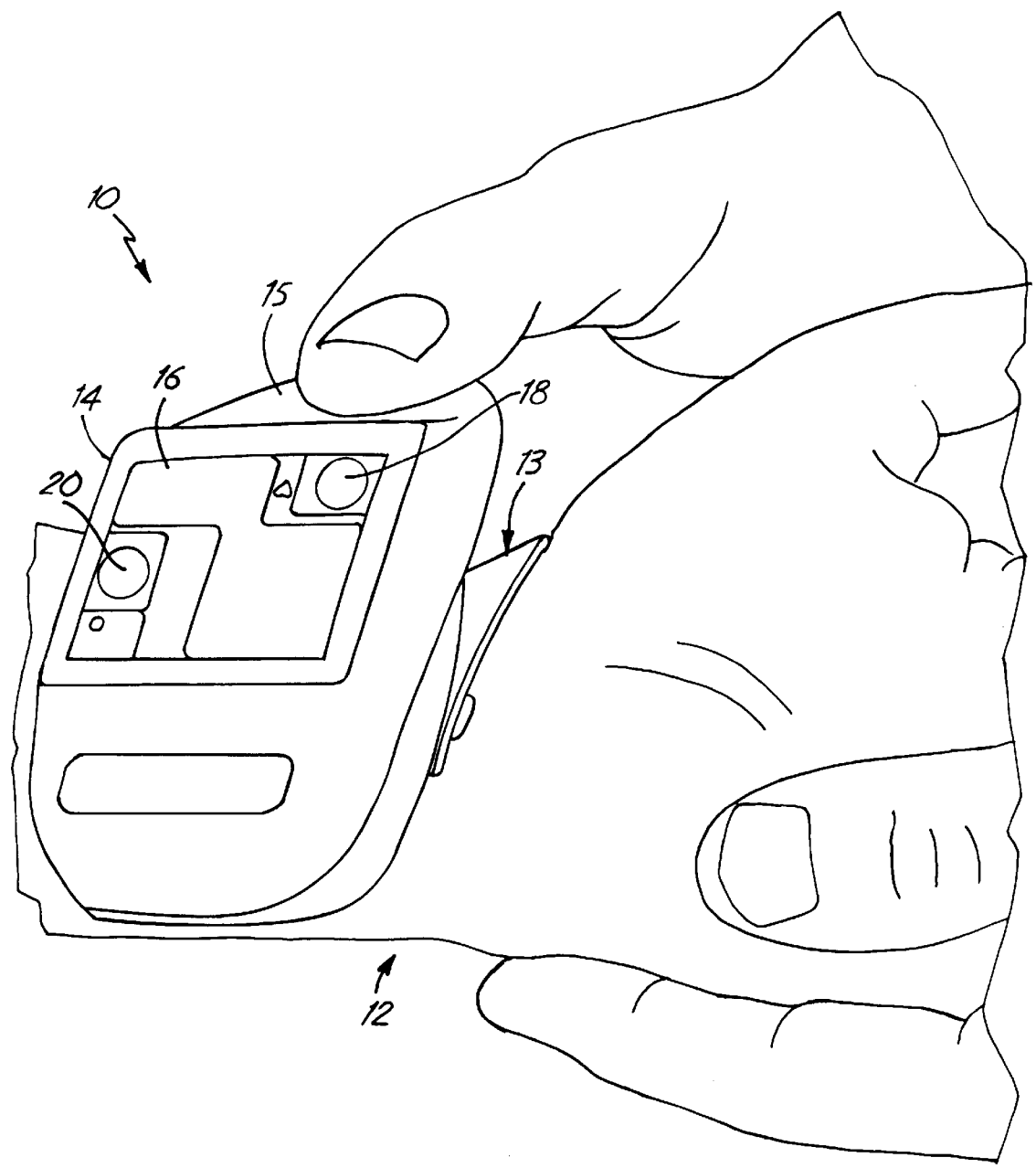
FIG. 1 is a perspective view of a preferred embodiment of a blood pressure measurement device of the present invention positioned over the wrist of a patient.

FIG. 1 illustrates a blood pressure measurement device being used to measure and display blood pressure within an underlying artery within wrist 12 of a patient. Blood pressure measurement device 10 includes placement guide 13, main housing 14, display panel 16, patient identification toggle 18, power switch 20, and sensor interface assembly 22 (best shown in FIGS. 2A and 2B).

Using placement guide 13 of measurement device 10, measurement device 10 is placed at the projection of the styloid process bone perpendicular to wrist 12. With device 10, a small amount of force is manually applied to the radial artery, which runs along the styloid process bone. As the force is manually applied, blood pressure waveforms are recorded and the corresponding hold down pressure which is being manually applied is also recorded. Using the shape of the blood pressure waveforms, waveform parameters are generated. These parameters, along with universal coefficients, are used to calculate pressure values which then can be displayed.

Placement guide 13 is connected to housing 14 at the base of housing 14. Placement guide 13 straddles the styloid process bone, automatically placing sensor interface assembly 22 over the underlying artery. Housing 14 contains all of the electrical components of measurement device 10. The shape and configuration of housing 14 allows it to hang on the patient's wrist, using placement guide 13 as a type of hook. Housing 14 includes pressure platform 15, which is a flattened depression directly above sensor interface assembly 22. In operation, the user (medical personnel) applies pressure on pressure platform 15 with a thumb or finger. The hold-down force from the user's thumb applies a force in an axial direction to wrist 12 of the patient. The axial force is transmitted from pressure platform 15 of housing 14 to sensor interface assembly 22.

In a preferred embodiment, display panel 16 simultaneously displays the following values based upon blood pressure measurements: systolic pressure, diastolic pressure, pulse rate, and mean blood pressure. Display panel 16 also preferably provides visual prompting for manually applying a varying hold down pressure.

Power switch 20 is actuated to turn on power to the circuitry within housing 14. Timing circuitry within housing 14 automatically turns power off after a predetermined period of inactivity. Actuation of switch 20, after the unit is turned on, causes display panel 16 to indicate previous readings of blood pressure and pulse rate.

Patient identification toggle 18 is used to organize the recorded blood pressure information with respect to a particular patient. After actuating power switch 20, the user selects the specific patient for which blood pressure will be measured by pressing patient identification toggle 18. In one embodiment, display panel 16 displays a patient identification number for the currently selected patient. The patient identification number changes as patient identification toggle 18 is pressed. In one embodiment the user can scroll through a list of 16 patient identification memory locations.

Figure 2A:
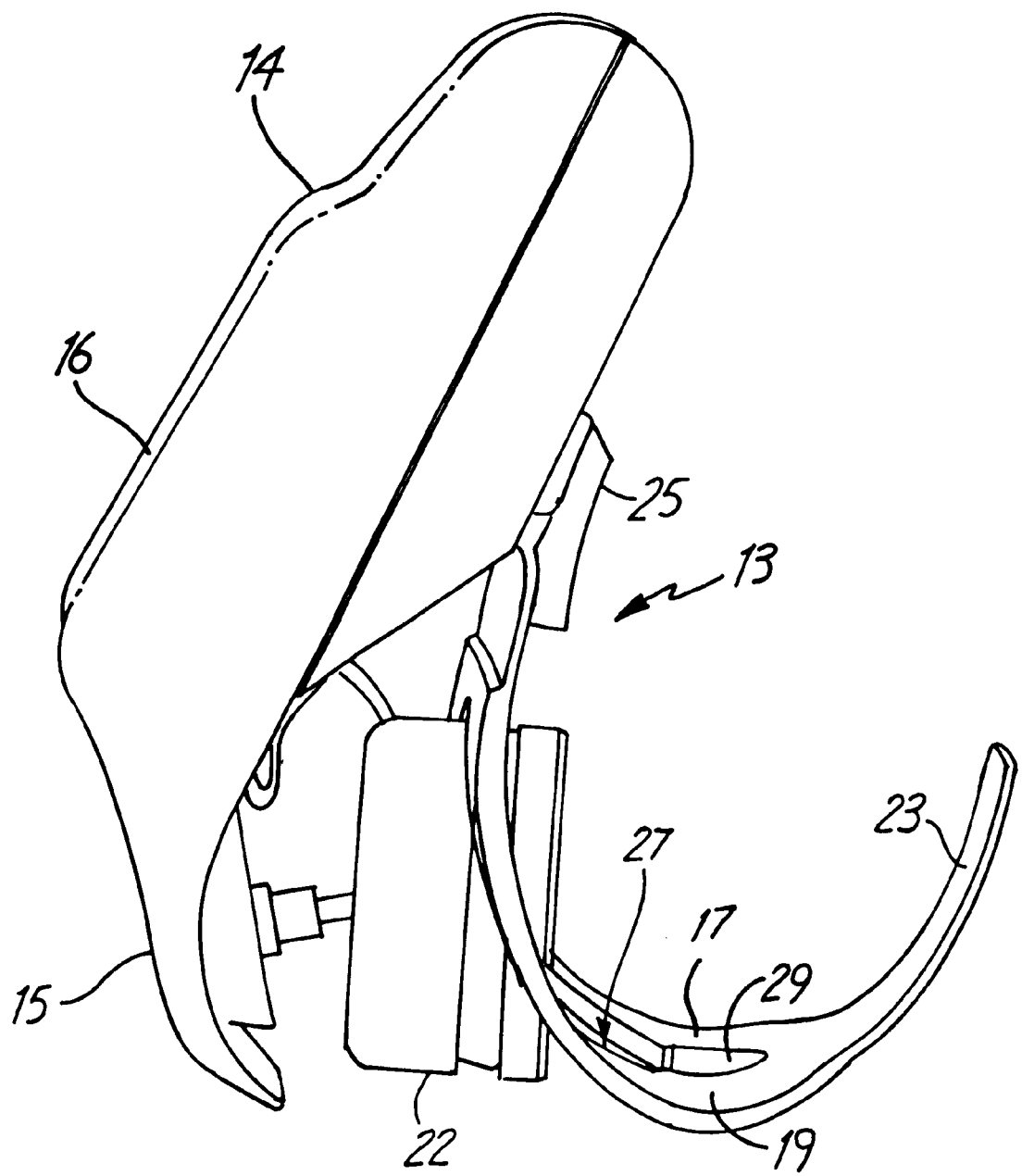
FIG. 2A is a side view of the blood pressure measurement device of FIG. 1.
Figure 2B:
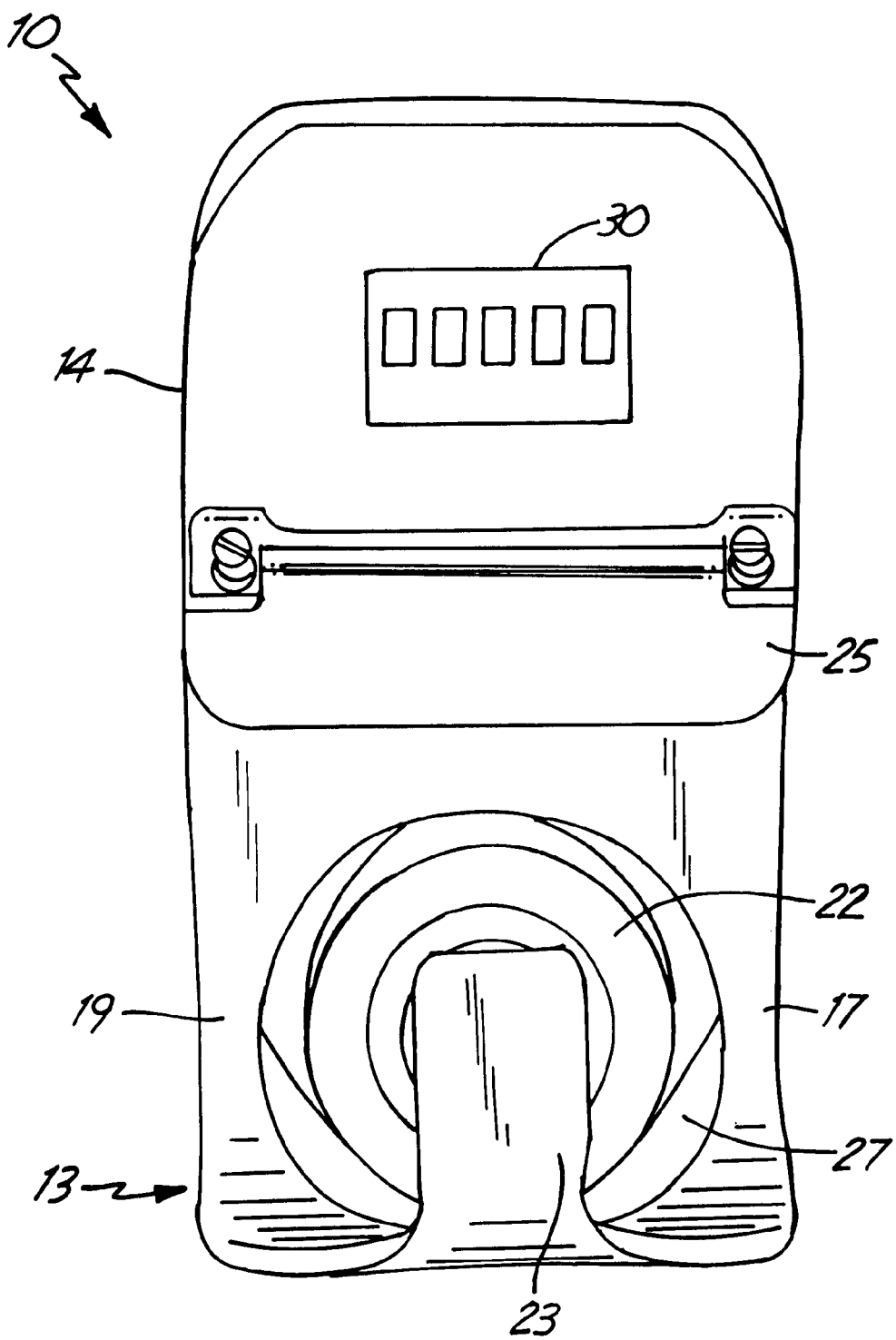
FIG. 2B is a bottom view of the blood pressure measurement device of FIG. 1.

FIG. 2A is a side view of blood pressure measurement device 10, and FIG. 2B is a bottom view of blood pressure measurement device 10. As can be seen from FIGS. 2A and 2B, placement guide 13 is generally U shaped. Placement guide 13 includes hook 23, pad 25, and opening 27. Opening 27 is a generally circular aperture that has a notch 29 near hook 23. Guide ribs 17 and 19 encircle opening 27 and notch 29, and meet at the base of hook 23.

When device 10 is placed on the patient, pad 25 contacts the palm side of the wrist of the patient, while hook 23 wraps around the backside of the wrist. Placement guide 13 is made of a flexible plastic so as to fit all patients, with the styloid process bone fitting into notch 29 of opening 27. Opening 27 also allows sensor interface assembly 22 to come in contact with the patient's wrist. Pad 25 becomes a pivot point about which force is applied.

Relying on a cantilever type action, device 10 allows the user to apply a force at pressure platform 15 of housing 14. Housing 14 pivots about pad 25, and sensor interface assembly 22 applies an axial force to the underlying artery. Sensor interface assembly 22 is pivotally mounted to housing 14. As pressure is manually applied by moving housing 14 toward the artery, that force is transferred from housing 14 to sensor interface assembly 22.

Device 10, with placement guide 13 and the cantilever type action, allows sensor interface assembly 22 to be consistently placed in the proper position, and the hold-down force to be consistently applied in the axial direction with respect to wrist 12. This improvement greatly simplifies the procedure of applying pressure by the user, because the user no longer controls the direction and angle at which pressure is applied with respect to the patient's wrist.

Instead of having to palpate wrist 12 to identify the location of the radial artery, a user simply places device 10 adjacent wrist 12 so that placement guide 13 hooks onto the patient's wrist with guide ribs 17 and 19 straddling the projection of the styloid process bone. The measurement process is significantly simplified with the present invention.

The force applied to the artery is swept in an increasing fashion so the pressure waveform data from a series of pulses are obtained with different amounts of force being applied. To achieve the desired pattern of variable force, user feedback is preferably provided with device 10.

In a preferred embodiment, feedback is in the form of a visual counter on display panel 16. As the user begins to apply pressure, a number is displayed corresponding to the amount of pressure applied by the user. As the user increases the applied pressure, the displayed number proportionally increases. The user (medical personnel) is previously instructed to increase pressure smoothly so that the displayed counter increases one integer at a time, approximately one per second. If the user increases the hold-down pressure too quickly, the displayed counter will also jump quickly through the corresponding numbers to indicate the choppy applied pressure. The user applies greater pressure until device 10 shows the resulting blood pressure measurements on display panel 16. Preferably, the user applies enough pressure to get the counter up to the number 15, but it could be as low as 4 or 5, or as high as 27 or 28, depending on the patient. If a patient has higher blood pressure, greater applied force will be necessary, and the corresponding ending counter number will be a higher integer.

After the measurement, the user can then view the blood pressure reading. In a preferred embodiment, display panel 16 provides a digital readout of systolic, diastolic, and mean blood pressure, as well as pulse rate. An indication of memory location (by number) corresponding to the patient is also displayed.

As soon as the reading is complete, device 10 is ready to take another reading. There is no need to clear display 16. Device 10 stores a predetermined number of previous readings (such as the last 10 readings). To review prior readings, patient identification toggle 18 or power switch 20 is pressed. This causes a different reading from memory to be displayed on display 16.

Alternatively, the feedback to the user can be audible tones and/or visual movable bars. The process of applying force in response to audible tones and/or visual movable bars on display 16 is fully described in U.S. Pat. No. 5,941,828, entitled "Non-Invasive Blood Pressure Sensor With Motion Artifact Reduction", which is incorporated herein.

As can be seen in FIG. 2B, device 10 includes external connector 30. External connector 30 is a five pin connector that is used to transmit and receive data, recharge battery 36 (see FIG. 3) contained within housing 14 and provide an alternative power source to device 10. External connector 30 allows device 10 to be connected to a docking station (not shown) so that its internal battery can be recharged, and the collected blood pressure information can be downloaded to a central system. Device 10 can be used by a nurse or other employee in a hospital setting to collect blood pressure and heart rate information from a series of patients.

After blood pressure and heart rate data are obtained, the nurse places device 10 into a docking station and a central computer (not pictured), which can transmit a command via external connector 30 to device 10. In response, device 10 outputs blood pressure and heart rate information, already organized with respect to particular patients (with the patient identification toggle 18), via external connector 30. Concurrently, the rechargeable battery 36 within device 10 is being recharged, and power is supplied to device 10 from the central computer (not pictured) via external connector 30, while device 10 is in the docking station (not pictured).

The central computer can then maintain a central database for all of the patients in the hospital, with the heart rate and blood pressure information automatically being downloaded into the database from device 10.

FIG. 3 is an electrical block diagram of device 10. Device 10 includes patient marker switch 18, power supply circuit 42, sensor interface assembly 22, connectors 58 and 60, amplifiers 62A and 62B, analog-to-digital (A/D) converter 64, microprocessor 68, display driver and memory circuit 82, display panel 16, non-volatile memory 78 and real-time clock 80. Power supply circuit 42 includes external connector 30, amplifiers 32 and 34, rechargeable battery 36, supply switch 38, reverse battery protection 40, switch 20, integrated power switch 44, OR circuit 46, voltage divider 48, analog regulator 50 and supervisor circuit 52.

Device 10 can be powered through an external power source. An external power source couples to device 10 through external connector 30. Power from external connector 30 on the VSUPPLY line causes supply switch 38 to disconnect rechargeable battery 36 from supplying power to supply circuit 42. Instead, rechargeable battery 36 is recharged using the CHRGR line while the external power source supplies power to supply circuit 42 on the VSUPPLY line. External connector 30 also allows device 10 to receive and transmit data, such as blood pressure information and device serial number, to an external device over the RX (receive) line and TX (transmit) line. The RX and TX lines are coupled to amplifiers 32 and 34, respectively, which amplify the signals transmitted and received by microprocessor 68. Amplifiers 32 and 34 are enabled when power is received through the VSUPPLY line, and are disabled when no power is received through the VSUPPLY line.

Switch 20 is partially a monitoring pushbutton switch. Pressing switch 20 causes OR circuit 46 to turn on integrated power switch 44. Integrated power switch 44 supplies power to all digital circuits, including microprocessor 68, display panel 16 and associated display driver and memory circuit 82. Integrated power switch 44 supplies power to microprocessor 68, which in turn latches on OR circuit 46. The turn off of the circuit is controlled by microprocessor 68 discontinuing a signal to OR circuit 46. This occurs through a fixed time of no activity.

Analog regulator 50 outputs electrical power which is used to energize analog circuitry, including amplifiers 62A and 62B, and analog-to-digital (A/D) converter 64.

Pressure transducers 56A and 56B and nonvolatile memory 54 within sensor interface assembly 22 are connected through connector 58 and connector 60 to circuitry within housing 14. Transducers 56A and 56B sense pressure communicated within sensor interface assembly 22 and supply electrical signals to connector 58. In a preferred embodiment, transducers 56A and 56B are piezoresistive pressure transducers. Nonvolatile memory 54 stores offsets of transducers 56A and 56B and other information such as a sensor serial number. Nonvolatile memory 54 is, in a preferred embodiment, an EEPROM.

The outputs of transducers 56A and 56B are analog electrical signals representative of sensed pressure. These signals are amplified by amplifiers 62A and 62B and applied to inputs of A/D converter 64. The analog signals to A/D converter 64 are converted to digital data and supplied to the digital signal processing circuitry 66 of microprocessor 68.

Microprocessor 68 includes digital signal processing circuitry 66, read only memory (ROM) and electrically erasable programmable read only memory (EEPROM) 70, random access memory (RAM) 72, timer circuitry 74, and input/output ports 76. A/D converter 64 may be integrated with microprocessor 68, while some of the memory may be external to microprocessor 68.

Based upon the pressure data received, microprocessor 68 performs calculations to determine blood pressure values. As each pulse produces a cardiac waveform, microprocessor 68 determines a peak amplitude of the waveform. Microprocessor 68 controls display driver 82 to create the visual counter on display 16 that counts in correlation to the hold down pressure applied by the user. The visual counter guides the user in applying a variable force to the artery.

When a measurement cycle has been completed, microprocessor 68 reorders the cardiac waveforms in increasing order of their corresponding hold down pressure and performs calculations to determine systolic pressure, diastolic pressure, mean blood pressure, and pulse rate. The process of calculating pressure using shape, amplitude, and hold down is described in the previously mentioned Medwave patents, which are incorporated by reference. If patient identification toggle 18 is pressed, a signal is supplied to microprocessor 68, causing it to toggle to a new pressure reading with a new memory location. In one embodiment, the memory location of that pressure reading is also displayed.

The blood pressure calculations, organized by patient, are preferably time-stamped at the time of calculation using real-time clock 80, and stored in nonvolatile memory 78, so that the calculations are not lost when power to device 10 is turned off. Non-volatile memory is preferably an EEPROM. As discussed above, the blood pressure information can then be transferred through external connector 30 to an external device. In a preferred embodiment, the sensor serial number is also output through external connector 30, so that blood pressure information can be organized with respect to particular measurement devices. The information output through external connector 30 may be stored on a computer and accessed through a local area network, the Internet, or other means.

Although the present invention has been described with reference to preferred embodiments, workers skilled in the art will recognize that changes may be made in form and detail without departing from the spirit and scope of the invention.

What is claimed is:

1. A device for sensing blood pressure of an underlying artery of a patient, the device comprising:

a housing having a sensing region and a pivot region, the housing pivotable about the pivot region in response to a hold down pressure applied at the sensing region by a user;

a pad supported by the pivot region for engaging a wrist of the patient, the pad forming a pivot point of the housing;

a sensor interface assembly supported by the sensing region, the sensor interface assembly having a sensing surface suited for engaging tissue adjacent the artery for sensing pressure from the artery; and a wrist connection for holding the housing adjacent the patient's wrist, the wrist connection including a substantially U-shaped member configured for sliding onto the patient's wrist wherein the pad is located at one end of the U-shaped member and the sensing region is spaced apart therefrom.

2. The device of claim 1, and further comprising a display for displaying pressure data as hold down pressure is applied by the user, the pressure data representing the magnitude of the pressure currently being applied by the user.

3. The device of claim 2, wherein the pressure data are integers ranging between 0 and an integer less than 30.

4. The device of claim 2, wherein the display further displays calculated systolic and diastolic pressures for a patient, and displays a patient identifier that identifies the patient corresponding to the calculated systolic and diastolic pressures.

5. The device of claim 1, wherein the sensor interface assembly is pivotally connected to the housing.

6. The device of claim 1, wherein the U-shaped member has an opening of sufficient size to allow the sensor interface assembly to pass through the opening and contact the patient's wrist.

7. The device of claim 6, wherein the wrist connection further comprises a notch formed in the U-shaped member, the device configured to consistently position the sensor interface assembly over the artery when the styloid process bone of the patient is positioned within the notch.

8. The device of claim 6, wherein the substantially U-shaped member is made of a flexible plastic to conform to the wrists of different patients.

9. The device of claim 1, wherein the sensing region of the housing includes a flattened depression positioned over the sensor interface assembly, the flattened depression providing a platform for receiving the hold-down pressure applied by the user.

10. The device of claim 1, and further comprising input means for entering patient identification data.

11. The device of claim 1, and further comprising an external connector for connecting the device to a second device, the device configured to transmit data to and receive data from the second device through the external connector.

12. The device of claim 11, wherein the device is rechargeable, the device being recharged by receiving power from an external power source through the external connector.

13. A device for sensing blood pressure of an underlying artery of a patient, the device comprising:

a cantilever housing having a proximal end and a distal end, the distal end having a base section that rests against a patient's wrist while a user applies a hold-down pressure at the proximal end;

a sensor interface assembly pivotally connected to the proximal end of the cantilever housing for sensing blood pressure information from the underlying artery;

connection means for holding the cantilever housing adjacent the patient's wrist wherein the connection means includes a hook to partially encircle the patient's wrist; and a pad supported by the base section and located at one end of the connection means, the pad for engaging the patient's wrist wherein the housing pivots about the pad.

14. The device of claim 13, and further comprising a display for displaying pressure data as hold down pressure is applied by the user, the pressure data representing the magnitude of the pressure currently being applied by the user.

15. The device of claim 14, wherein the pressure data are integers ranging between 0 and an integer less than 30.

16. The device of claim 14, wherein the display further displays calculated systolic and diastolic pressures for a patient, and displays a patient identifier that identifies the patient corresponding to the calculated systolic and diastolic pressures.

17. The device of claim 13, wherein the sensor interface assembly is pivotally connected to the cantilever housing.

18. The device of claim 13, wherein the hook has an opening of sufficient size to allow the sensor interface assembly to pass through the opening and contact the patient's wrist.

19. The device of claim 18, wherein the hook is made of a flexible plastic to conform to the wrists of different patients.

20. The device of claim 13, wherein the connection means further comprises positioning means for consistently positioning the sensor interface assembly over the artery.

21. The device of claim 13, wherein the proximal end of the cantilever housing includes a flattened depression positioned over the sensor interface assembly, the flattened depression providing a platform for receiving the hold-down pressure applied by the user.

22. The device of claim 13, and further comprising input means for entering patient identification data.

23. The device of claim 13, and further comprising an external connector for connecting the device to a second device, the device configured to transmit data to and receive data from the second device through the external connector.

24. The device of claim 23, wherein the device is rechargeable, the device being recharged by receiving power from an external power source through the external connector.

25. A method for determining blood pressure of an artery having a pulse, the method comprising:

applying pressure to the artery using cantilever action;

sensing pressure waveform data produced by the artery;

deriving a plurality of parameters from the pressure waveform data; and determining a blood pressure value based upon the parameters.

26. A method for measuring blood pressure of an artery using a non-invasive blood pressure measurement device, the method comprising:

placing a U-shaped member of the blood pressure measurement device on a wrist of a patient to position a sensing surface over the artery;

pivoting the blood pressure measurement device about a fulcrum to apply a force to the artery;

sensing pressure waveform data produced by the artery; and determining a blood pressure value based on the sensed pressure waveform data.

* * * * *